United States Patent [19]
Savidge et al.

[11] 3,974,442
[45] Aug. 10, 1976

[54] SURFACE DEFECT PROBE AND DUAL CHANNEL APPARATUS WITH LIFTOFF COMPENSATION

[75] Inventors: David Harvey Savidge; Eric Wadsworth, both of Rotherham, England

[73] Assignee: British Steel Corporation, London, England

[22] Filed: June 25, 1975

[21] Appl. No.: 590,194

[30] Foreign Application Priority Data
June 27, 1974  United Kingdom............... 28597/74

[52] U.S. Cl. .................................................. 324/37
[51] Int. Cl.² .......................................... G01R 33/12
[58] Field of Search ................................. 324/37, 40

[56] References Cited
UNITED STATES PATENTS

| | | | |
|---|---|---|---|
| 2,744,233 | 5/1956 | Paivenen.............................. | 324/40 |
| 2,985,824 | 5/1961 | Renken, Jr........................... | 324/37 |
| 3,358,225 | 12/1967 | Peugeot............................... | 324/40 |
| 3,611,120 | 10/1971 | Forster................................ | 324/37 |

OTHER PUBLICATIONS
Allen, J. W., Eddy Current Testing in Practice, Oak Ridge Nat. Lab. Publication No. 2655, Apr. 30, 1959, pp. 18–26.

*Primary Examiner*—Robert J. Corcoran
*Attorney, Agent, or Firm*—Bacon & Thomas

[57]  ABSTRACT

Apparatus for detecting surface defects in steel billets comprises an h.f. energized eddy current probe for scanning over the surface of the billet and a dual channel receiver responsive to signals from this probe dependent on (a) any surface defects, and (b) the probe surface spacing, in a manner such that in one channel a predominant factor in the signal waveform is characteristic of (a) while in the other channel a predominant factor in the signal is characteristic of (b). The signals from the two channels are combined in a summing amplifier and a difference amplifier whereby the outputs therefrom are conditioned to be exclusively characteristic of (a) and (b) respectively.

10 Claims, 6 Drawing Figures

SURFACE DEFECT PROBE AND DUAL CHANNEL APPARATUS WITH LIFTOFF COMPENSATION

This invention relates to a surface defect detector, and particularly, but not exclusively, relates to such detectors for detecting defects in the surface of steel billets.

This invention consists in apparatus for detecting surface defects in an elongate metallic member, comprising a high frequency energised eddy current probe for scanning over the surface of the member, a dual-channel receiver responsive to signals from this probe dependent on (a) any surface defects, and (b) the probe-surface spacing in a manner such that in one channel a predominant factor in the signal waveform is characteristic of (a) whilst in the other channel a predominant factor in the signal is characteristic of (b), and means for combining the signals from the two channels in a summing amplifier and a difference amplifier, respectively, whereby the signal outputs therefrom are conditioned to be exclusively characteristic of (a) and (b), respectively.

Preferably, the spacing signal (b) from the difference amplifier is operative on the defect signal (a) from the summing amplifier whereby to compensate the latter for changes in sensitivity resulting from changes in the probe-surface spacing during scanning.

For calibration purposes, a bias signal is conveniently applied as an additional input to the difference amplifier whereby to provide zero output therefrom when the probe is in free air.

For rectangular-section members viz. billet or slab, one or more probes may be mounted on the periphery of a disc rotatable over the surface about an axis perpendicular thereto, but where the member is of circular section the probe(s) may be mounted in a sensing head rotatable about the circular surface. In both cases the inspection pattern defined will be dependent on the rotational speed of the head and the axial speed of throughput.

The probe itself may form the inductive part of a tuned oscillator circuit thus avoiding the stray capacitance problems associated with this item at the high operating frequencies employed, e.g. 5 MHz to 10 MHz. By incorporating the probe coil in the tuned circuit in this fashion the coil parameters are thereby resolved into an in-phase component (resistance) and a quadrature component (inductance), subsequent recombination of these components after further processing being designed to reject unwanted information of a particular phase angle, i.e., representative of factors (a) or (b) above, in a manner analogous to phase sensitive systems.

In order that the invention may be fully understood one embodiment thereof will not be described, by way of example, with reference to the accompanying drawings in which.

Figure 1:
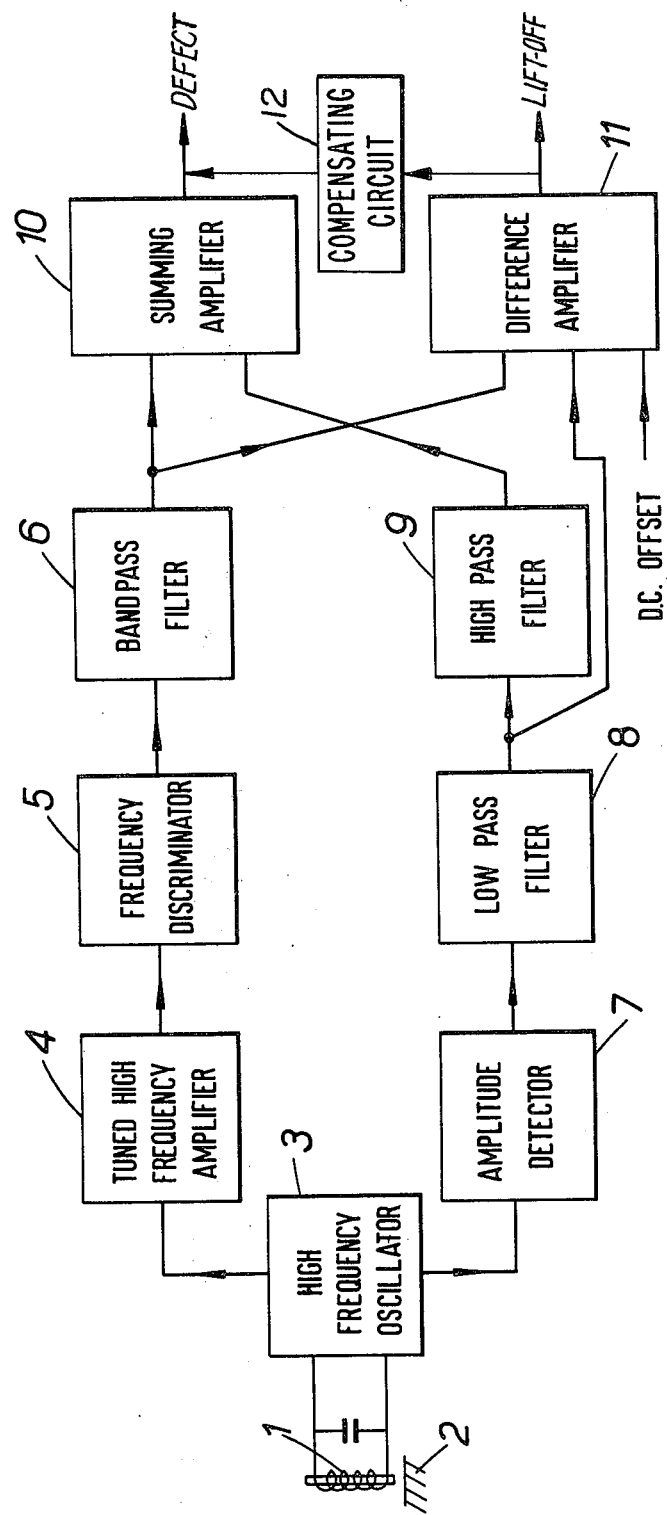
FIG. 1 is a block circuit diagram of apparatus according to this invention.

Referring firstly to FIG. 1 of the drawings, the coil 1 in the probe head traverses the surface of a steel billet 2 and is energised by a high frequency oscillator 3 operating at, e.g. 5 MHz.

The varying magnetic field induced in the billet introduces eddy currents any change in the path of which, occasioned, e.g. by a defect, will be reflected in a change in the amplitude and the frequency of the oscillator output. Whilst both the amplitude and the frequency content will be dependent on both the probe-surface spacing and surface defects, the amplitude content will be primarily dependent on probe-surface spacing whereas the frequency content will be more dependent on surface defects than the spacing (lift-off) factor. In particular, in regard to the latter, the eddy currents introduced into the billet generate a magnetic field opposing that from the coil, the resultant change in inductance causing a change in frequency.

The 'frequency' information is fed to a tuned high frequency amplifier 4 designed to accept the range of frequencies produced by the probe coil and the output therefrom is then decoded by a frequency discriminator 5 to produce a signal output proportional to the input frequency. This signal is applied to a band-pass filter 6 which is designed to accept only those signals within a given phase band which are typical of those produced by surface defects and lift-off conditions.

The information relating to amplitude is fed to a detector 7 and then to a low-pass filter 8 the higher frequencies accepted by this filter then being passed through a succeeding high-pass filter 9; in effect filters 8 and 9 together operate as a band-pass filter.

Figure 2A:
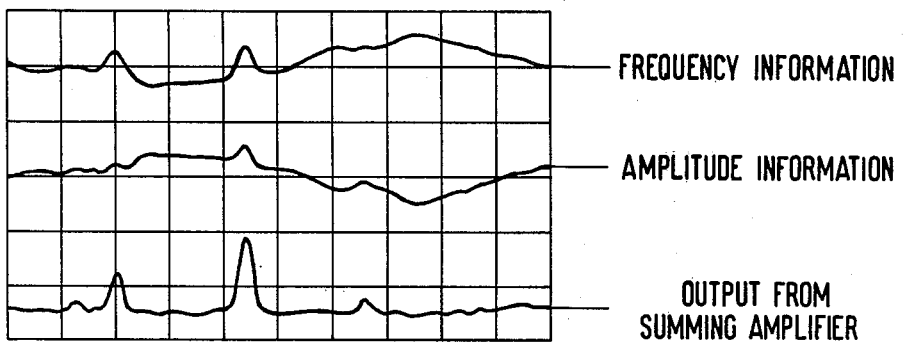
FIGS. 2a and 2b are wave-form diagrams showing the input and output signals at the summing and difference amplifiers in FIG. 1.
Figure 2B:
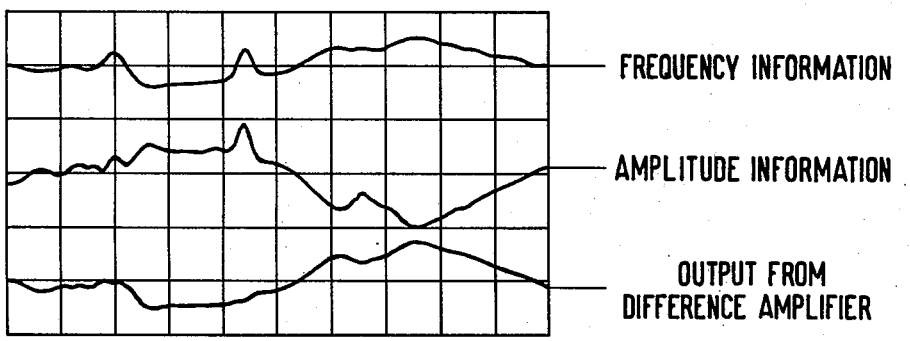

The output from the latter is applied, together with the 'frequency' output from the band-pass filter 6, to an a.c. coupled summing amplifier 10 where the two signals are summated, the resultant output then being essentially indicative solely of the 'defect' content. Typical input and output waveforms at this amplifier are shown in FIG. 2 (a) from which it can be seen that a predominant characteristic of the upper waveform is the high frequency 'peaks' whereas these peaks are less noticeable in the lower waveform, where the predominant characteristic is the amplitude information.

In a similar fashion the frequency information from the band-pass filter is fed to a difference amplifier 11, together with the amplitude information from the low-pass filter 8. The difference between these two signals is a signal essentially indicative solely of the probe-surface spacing. Typical input and output waveforms at this amplifier are shown in FIG. 2 (b). Additionally however a d.c. off-set is introduced designed to produce zero output from this amplifier when the probe coil is in free air.

The outputs from the summing and difference amplifiers are therefore representative of surface defects and 'lift-off' respectively, but since the amplitude of the former signal is still dependent on the separation between the coil and the billet surface the lift-off signal (b) can be used by a compensating circuit 12 to compensate the defect signal for any gain or loss in sensitivity as the probe clearance changes by further circuitry.

Accurate and positive identification of defects in the billet surface is thus effected and provision may readily be made for this signal to be utilised for marking the defective area to permit the defect to be physically removed, e.g. by grinding; this aspect is however part of the present invention.

Figure 3:
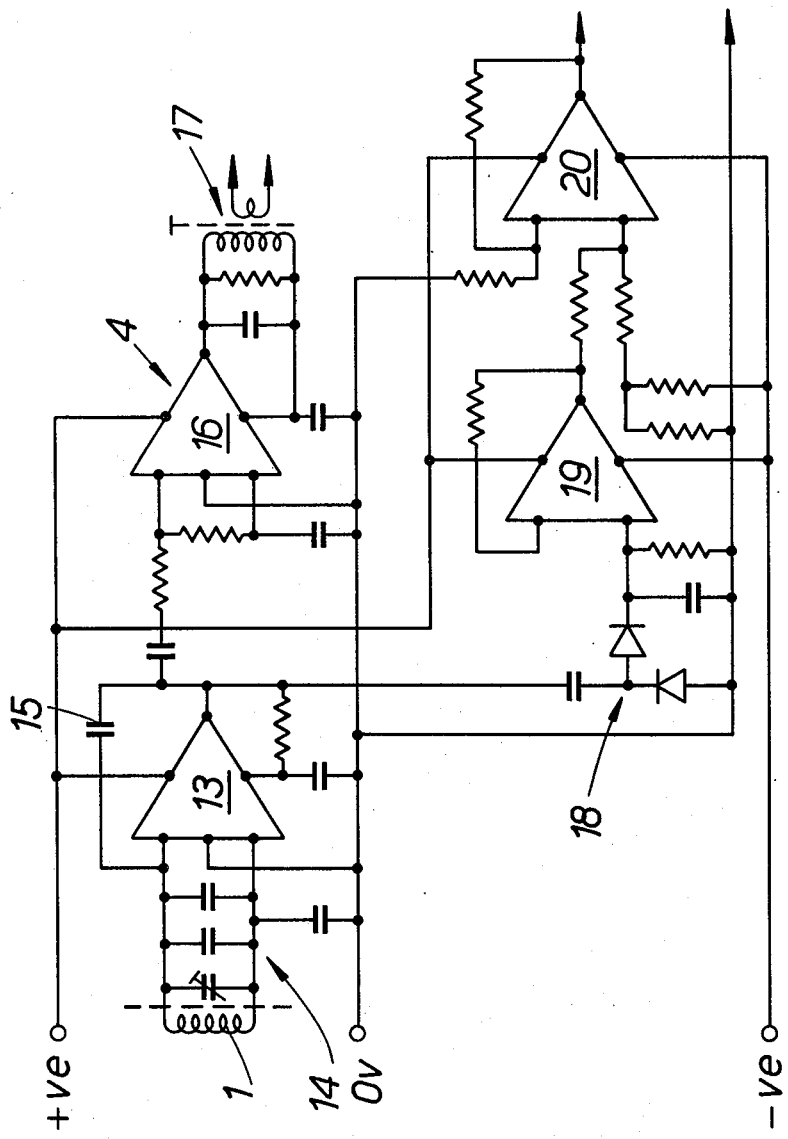
FIG. 3 is a circuit diagram of the oscillator/coil combination shown in FIG. 1.

As mentioned above, the probe coil forms the inductive part of the high frequency oscillator 3 and the circuit diagram of this unit together with the tuned h.f. amplifier 4 and the amplitude detector are shown in detail in FIG. 3.

Referring now to this figure, the oscillator itself (13), e.g. an integrated circuit type LM 703L, has a tuned circuit comprising the probe coil 1 and tuning capacitors 14. The oscillator produces a constant current feed to the coil so that the amplitude of the voltage developed across it will be determined by the resistive properties of the coil impedance and the frequency of oscillation will be determined by the reactive component of the coil impedance.

The output from the oscillator, which is sustained by a feedback capacitor 15, is R.C. coupled to the tuned h.f. amplifier 4 which comprises an integrated circuit 16 of the same type as the circuit 13. This acts as a 'buffer' amplifier and an amplitude limiter, and the characteristic frequency information is transformer coupled at 17 and then applied to the frequency discriminator 5 (FIG. 1).

The oscillator output is also applied to the amplitude detector 7 through a diode unit 18, the output from this unit defining a unidirectional 'envelope' of the alternating output. This signal is amplified in an l.f. operational amplifier 19 and is applied to a like amplifier 20 which is designed to add a fixed negative voltage to the signal from the amplifier 19 and thereby reduce the d.c. offset that would have been produced at the output of amplifier 20. Both amplifiers 19 and 20 may conveniently be i.c's type 741C.

Figure 4:
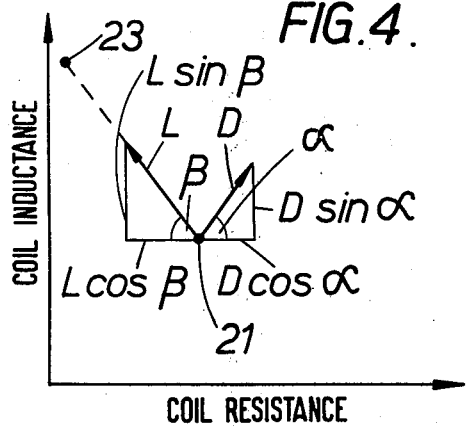
FIG. 4 is an impedance diagram showing the phase relationship between various components of signals derived from the probe coil.

FIG. 4 is a phase diagram from which the operation of this circuit might be better understood. In particular, point 21 on this diagram is indicative of the impedance of the coil when it is positioned close to a specimen billet. The vector L identifies the changes in the inductance and resistance of the coil as the coil moves away from the specimen, the point 23 indicating the coil impedance in free air; i.e. the vector L is the lift-off vector. Vector D is the defect vector, that is, it identifies changes in the inductance and resistance of the coil as it traverses faults in the specimen of varying intensities and relates to a constant operating clearance or lift-off.

The changes in coil inductance as the billet is scanned, i.e., the frequency information, are proportional to the expression $L \sin \beta + D \sin \alpha$, that is, both these quantities 'move' in the same direction, they are additive. On the other hand changes in the coil resistance, i.e., the amplitude information, are proportional to the expression $- L \cos \beta + D \cos \alpha$; in this instance the components are substractive. As described above, the addition and subtraction of the above expressions are performed by the circuits 10 and 11, respectively, to produce separate signals which exclusively relate to defect and lift-off. These latter circuit modules together with the filter circuits mentioned are all of standard construction.

Figure 5:
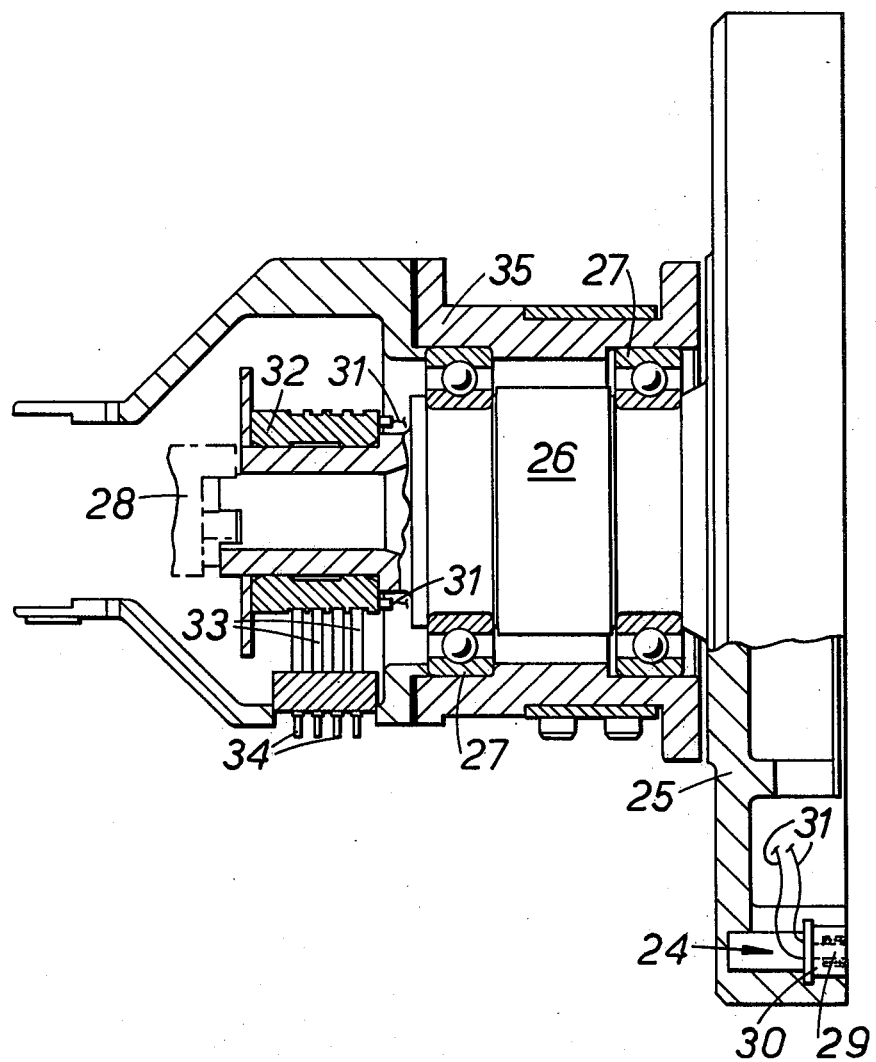
FIG. 5 shows one particular form of scanning head.

The mechanical construction of a typical sanning head for traversing the side of a billet is shown in FIG. 5.

In this drawing two diametrically opposed probe coils 24 (only one of which is shown) are mounted in a disc-shaped body 25 having a shaft 26 mounted for rotation in bearings 27. In turn this is coupled to a flexible drive system 28. The coil in each probe is wound on a ferrite core 29 which is mounted in a cup-shaped ferrite surround 30, the coil then being potted-in. The leads (31) from the coil are channelled through the head to separate slip rings in a unit 32 carried on the rear end of the shaft 26.

Resilient connectors 33 bear on the slip ring contacts and these are separately coupled to terminals 34 in a support mounting 35 from which the signal outputs are fed to the circuitry described above.

Four of such heads would be required for scanning all sides of a billet on one pass.

Although this invention has been described with reference to the particular embodiment illustrated, it is to be understood that various modifications may be made without departing from the scope of this invention. For example, details of the circuits shown may readily be changed provided that their overall function remains the same. The probe head itself may also be differently designed, the one shown simply being convenient for the task involved. Similarly, the scanning head may incorporate only one probe coil, or alternatively more than two could be provided, the more probe coils there are the greater the degree of surface coverage for a given rotational speed and axial speed of billet throughput.

We claim

1. Apparatus for detecting surface defects in an elongate metallic member, comprising
    a high frequency energised eddy current probe for scanning over the surface of the member,
    a dual-channel receiver responsive to signals from this probe dependent on (a) any surface defects and (b) the probe-surface spacing in a manner such that in one channel a predominant factor in the signal waveform is characteristic of (a) whilst in the other channel a predominant factor in the signal is characteristic of (b),
    a summing amplifier,
    a difference amplifier and
    circuit means for combining the signals from the two channels in the summing amplifier and the difference amplifier, respectively, whereby the signal outputs therefrom are conditioned to be exclusively characteristic of (a) and (b), respectively.

2. Apparatus according to claim 1 comprising a compensating circuit responsive to the spacing signal (b) from the difference amplifier and operative on the defect signal (a) from the summing amplifier for compensating the latter for changes in sensitivity resulting from changes in the probe-surface spacing during scanning.

3. Apparatus according to claim 2, comprising
    a bias signal source, the bias signal therefrom being supplied as an additional input to the difference amplifier whereby to provide zero output therefrom when the probe is in free air.

4. Apparatus according to claim 3, comprising
    a constant current high frequency tuned oscillator by which the eddy current probe is energised, said probe comprising
    a coil which forms the inductive part of the tuned circuit of said oscillator.

5. Apparatus according to claim 4, wherein the dual-channel receiver comprises, in series in the defect channel,
    a high frequency amplifier operable as a buffer and an amplitude limiter,
    a frequency discriminator and a band pass filter, and wherein the oscillator output is resistance-capacitance coupled to the high frequency amplifier.

6. Apparatus according to claim 4, wherein the dual-channel receiver comprises, in series in the spacing channel, an amplitude detector and a filter circuit, and wherein the oscillator output is diode coupled to the amplitude detector.

7. Apparatus according to claim 4, for detecting defects in a rectangular section bar, comprising a disc rotatable over a surface of said bar about an axis perpendicular to said surface, a separate disc being provided for each surface, and wherein at least one probe is mounted in each disc.

8. Apparatus for detecting surface defects in a steel billet comprising a high frequency energised eddy current probe for scanning over the billet surface, a dual-channel receiver responsive to signals from the probe dependent on (a) any surface defects and (b) the probe-surface spacing and including, in series in one channel a high frequency amplifier, a frequency discriminator and a band-pass filter, a predominant factor in the output therefrom being characteristic of (a) and in series in the other channel an amplitude detector and a filter circuit, a predominant factor in the output therefrom being characteristic of (b), a summing amplifier, a difference amplifier and circuit means for combining the outputs of the two channels in the summing amplifier and the difference amplifier whereby the signal outputs therefrom are exclusively characteristic of (a) and (b), respectively.

9. Apparatus according to claim 8, wherein said filter circuit comprises a low pass filter, the output therefrom being applied to said difference amplifier and a filter for passing the higher frequencies from said low pass filter to said summing amplifier.

10. Apparatus according to claim 9, comprising a bias signal source, the bias signal therefrom being applied as an additional input to the difference amplifier whereby to provide zero output therefrom when the probe is in free air.

* * * * *